US011279667B2

United States Patent
Krill et al.

(10) Patent No.: US 11,279,667 B2
(45) Date of Patent: Mar. 22, 2022

(54) CATALYST FOR THE OXIDATIVE ESTERIFICATION OF ALDEHYDES TO CARBOXYLIC ESTERS

(71) Applicant: Roehm GmbH, Darmstadt (DE)

(72) Inventors: Steffen Krill, Muehltal (DE); Marcel Treskow, Darmstadt (DE)

(73) Assignee: Roehm GmbH, Darmstadt (DE)

( * ) Notice: Subject to any disclaimer, the term of this patent is extended or adjusted under 35 U.S.C. 154(b) by 0 days.

(21) Appl. No.: 16/134,569

(22) Filed: Sep. 18, 2018

(65) Prior Publication Data

US 2019/0084914 A1   Mar. 21, 2019

(30) Foreign Application Priority Data

Sep. 19, 2017   (EP) .................................... 17191731

(51) Int. Cl.
| | | |
|---|---|---|
| *C07C 67/44* | (2006.01) | |
| *B01J 35/00* | (2006.01) | |
| *B01J 37/02* | (2006.01) | |
| *C07C 67/39* | (2006.01) | |
| *B01J 37/18* | (2006.01) | |
| *B01J 21/04* | (2006.01) | |
| *B01J 21/06* | (2006.01) | |
| *B01J 21/08* | (2006.01) | |
| *B01J 23/52* | (2006.01) | |
| *B01J 23/80* | (2006.01) | |
| *B01J 35/02* | (2006.01) | |
| *B01J 35/10* | (2006.01) | |
| *C07C 69/54* | (2006.01) | |

(52) U.S. Cl.
CPC ............... *C07C 67/44* (2013.01); *B01J 21/04* (2013.01); *B01J 21/063* (2013.01); *B01J 21/066* (2013.01); *B01J 21/08* (2013.01); *B01J 23/52* (2013.01); *B01J 23/80* (2013.01); *B01J 35/006* (2013.01); *B01J 35/008* (2013.01); *B01J 35/023* (2013.01); *B01J 35/1014* (2013.01); *B01J 35/1019* (2013.01); *B01J 35/1061* (2013.01); *B01J 37/0201* (2013.01); *B01J 37/0236* (2013.01); *B01J 37/18* (2013.01); *C07C 67/39* (2013.01); *C07C 69/54* (2013.01)

(58) Field of Classification Search
CPC ......... C07C 67/44; C07C 67/39; C07C 69/54; B01J 21/04; B01J 21/063; B01J 21/066; B01J 21/08; B01J 23/52; B01J 23/80; B01J 35/006; B01J 35/008; B01J 35/023; B01J 35/1014; B01J 35/1019; B01J 35/1061; B01J 37/0201; B01J 37/0236; B01J 37/18

See application file for complete search history.

(56) References Cited

U.S. PATENT DOCUMENTS

| | | | |
|---|---|---|---|
| 4,283,564 A | 8/1981 | Bernhagen et al. | |
| 4,496,770 A | 1/1985 | Duembgen et al. | |
| 5,969,178 A | 10/1999 | Okamoto et al. | |
| 6,040,472 A | 3/2000 | Yamamatsu et al. | |
| 7,012,039 B2 | 3/2006 | Watanabe et al. | |
| 9,617,199 B2 | 4/2017 | Krill et al. | |
| 9,732,023 B2 | 8/2017 | Balduf et al. | |
| 9,890,105 B2 | 2/2018 | Krill et al. | |
| 9,963,417 B2 | 5/2018 | Krill et al. | |
| 10,125,077 B2 | 11/2018 | Krill et al. | |
| 2003/0060655 A1* | 3/2003 | Hayashi | B01J 23/52 560/238 |
| 2010/0249448 A1* | 9/2010 | Suzuki | B01J 23/892 560/208 |
| 2016/0068464 A1* | 3/2016 | Krill | C07C 45/75 560/208 |
| 2018/0001307 A1* | 1/2018 | Lygin | B01J 37/0236 |
| 2018/0326400 A1* | 11/2018 | Lygin | B01J 37/06 |

FOREIGN PATENT DOCUMENTS

| | | |
|---|---|---|
| DE | 28 55 504 | 6/1980 |
| EP | 0 092 097 | 10/1983 |
| EP | 1 393 800 A1 | 3/2004 |
| EP | 2 177 267 A1 | 4/2010 |
| EP | 2 210 664 A1 | 7/2010 |
| EP | 3 170 558 A1 | 5/2017 |

(Continued)

OTHER PUBLICATIONS

Haruta et al., "Low-Temperature Oxidation of CO over Gold Supported . . . ", J. Catal. 1993, vol. 144, pp. 175-192.

Xiaoyue Wan, et al., "Magnesia-supported gold nanoparticles as efficient . . . ", Catalysis today, 233, 2014, S. 147 (Tab. 1).

Charlotte Marsden, et al., "Aerobic oxidation of aldehydes under . . . ", Green Chem., 2008, 10, 168-170.

http://www.mintek.co.za/Mintek75/Proceedings/J04-McPherson.pds.

(Continued)

*Primary Examiner* — Sheng H Davis
*Assistant Examiner* — Michael Forrest
(74) *Attorney, Agent, or Firm* — Oblon, McClelland, Maier & Neustadt, L.L.P.

(57) ABSTRACT

The present invention relates to a novel process for oxidative esterification, generally for reaction of aldehydes with alcohols in the presence of oxygenous gases directly to give the corresponding ester in the presence of a heterogeneous catalyst, by means of which, for example, (meth)acrolein can be converted to methyl (meth)acrylate. The new catalyst has titanium dioxide as the main component of the support material. The catalysts are especially notable for high mechanical and chemical stability and for good catalytic performance even over very long periods. The process is an improvement in the catalyst service life, activity and selectivity over prior art catalysts which lose activity and/or selectivity relatively quickly in continuous operation in media having even a small water content.

12 Claims, 4 Drawing Sheets

(56) References Cited

FOREIGN PATENT DOCUMENTS

| WO | WO-2014170223 A1 | * | 10/2014 | ............. C07C 45/75 |
| WO | WO-2016113106 A1 | * | 7/2016 | .......... B01J 37/0236 |
| WO | 2017/084969 A1 | | 5/2017 | |

OTHER PUBLICATIONS

Ken Suzuki, et al., "Aerobic Oxidative Esterification of Aldehydes . . . ", ACS Catalysis., 3(8), 2013, S. 1845.

Koichi Nagai, et al., "Trends and Future of Monomer—MMA Technologies", Sumitomo Basic Chem. Research Lab. (http://www.sumitomo-chem.co.jp/english/rd/report/theses/docs/20040200_30a.pdf).

Ullmann's Encyclopedia of Industrial Chemistry 2012, Methacrylic Acid from Ethylene.

Yuchao Li, et al., "Oxidative Esterification of Methacrolein . . . ", CHEMCATCHEM, Bd 9, Nr. 11, p. 1960-1968.

Shota Kenjo, et al., "Alkoxylation of alpha, beta-unsaturated aldehydes . . . ", Microporous and Mesoporous Materials, Bd. 237, 10, p. 12-22.

U.S. Appl. No. 15/543,291, filed Jul. 13, 2017, US 2018-0001307 A1, Lygin et al.

U.S. Appl. No. 15/776,837, filed May 17, 2018, US 2018-0326400 A1, Lygin et al.

U.S. Appl. No. 16/095,065, filed Oct. 19, 2018, Lygin et al.

U.S. Appl. No. 16/611,546, filed Nov. 7, 2019, Alexander Lygin et al.

\* cited by examiner

CATALYST FOR THE OXIDATIVE ESTERIFICATION OF ALDEHYDES TO CARBOXYLIC ESTERS

CROSS REFERENCE TO RELATED APPLICATION

This application claims the benefit of the European patent application EP 17191731, filed Sep. 19, 2017, the entire disclosure of which is incorporated herein by reference.

FIELD OF THE INVENTION

The present invention relates to a novel process for oxidative esterification, generally for reaction of aldehydes with alcohols in the presence of oxygenous gases directly to give the corresponding ester in the presence of a heterogeneous catalyst, by means of which, for example, (meth) acrolein can be converted to methyl (meth)acrylate. The catalysts used for this purpose in accordance with the invention are especially notable for high mechanical and chemical stability and for good catalytic performance even over very long periods. This especially relates to an improvement in the catalyst service life, activity and selectivity over prior art catalysts which lose activity and/or selectivity relatively quickly in continuous operation in media having even a small water content. What is special about this new catalyst according to the invention is that it has titanium dioxide as the main component of the support material. A further important aspect is the suppression and significant reduction of the formation of by-products that boil close to the desired ester, especially methyl methacrylate, or form azeotropes with the product or the reactants that are difficult to separate. The novel catalyst type thus allows production of MMA purities and qualities much higher than with the catalysts described to date in the prior art.

BACKGROUND

The catalytic oxidative esterification of aldehydes for preparation of carboxylic esters is described extensively in the prior art. For example, it is possible in this way to prepare methyl methacrylate very efficiently from methacrolein (MAL) and methanol. U.S. Pat. Nos. 5,969,178 and 7,012,039 in particular describe a process for continuously preparing MMA from isobutene or tert-butanol. This process has the following steps: 1) oxidation of isobutene or tert-butanol to methacrolein and 2) direct oxidative esterification of MAL with methanol to give MMA with a Pd—Pb catalyst on an oxidic support. Even though conversion and selectivity are high in principle, it is necessary to constantly supply a lead component for continuous operation since the catalyst has a continuous low loss of lead ions. The workup and removal of lead-containing wastewaters entail great technical complexity and ultimately also cause critical heavy metal-containing waste materials and wastewaters.

However, all the catalysts known from the prior art have a relevant loss of selectivity and/or activity over the course of prolonged service lives. For example, EP 1 393 800 describes good activities and selectivities, but at the same time no information is given as to the lifetime of the catalysts. Some of these are gold-containing catalysts, the catalytic gold particles described as active oxidation species especially having an average diameter of less than 6 nm. Said gold particles are distributed over a silicon oxide support or a $TiO_2/SiO_2$ support. As additional active components apart from gold, such catalysts also comprise other metals inter alia. A synergistic and activity- and selectivity-enhancing effect is ascribed to these doping components, but they also make the catalyst production complex and difficult to reproduce.

The preparation is effected by applying the gold salt and further metal salts to an oxidic support and a subsequent thermal treatment in the presence of hydrogen as reducing agent. For the conversion of pyruvaldehyde to ethyl pyruvate, for example, one catalyst described is a gold- and cobalt-containing catalyst on a $TiO_2$ support. In this catalyst, cobalt is present in metallic form {Co(0)}. The selectivity for the target product (ethyl pyruvate) in this case is 81% with a space-time yield of 24 mol/kg cath. The selectivities of other gold-containing catalysts (without cobalt) for MMA at a content of 4.5% by weight of Au are reported to be up to 93%, and the space-time yield is reported to be up to 50.7 mol of MMA/kg cath. Naturally, the use of such high gold loadings for achievement of high space-time yields is associated with considerable costs in catalyst production.

Haruta et al. in J. Catal. 1993, Vol. 144, pp 175-192 state that gold nanoparticles applied to transition metal oxide supports, such as $TiO_2$, $Fe_2O_3$ or $Co_3O_4$, are active oxidation catalysts. In this case, an interaction between gold and transition metal plays a crucial role for the catalyst activity.

U.S. Pat. No. 6,040,472 describes alternative catalysts, but these lead only to inadequate activities and selectivities for MMA by comparison. In this case, the catalysts are Pd/Pb-containing catalysts having a shell structure. The selectivities for MMA are reported to be up to 91%, and the space-time yield is reported to be up to 5.3 mol. Here too, lead doping is crucial for the formation of the active oxidation species, but creeping loss of lead ions results in the above-described drawbacks, and the catalyst production is comparatively complicated, one particular reason for which is the use of critical lead salts in the impregnation.

EP 2 177 267 and EP 2 210 664 describe nickel-containing catalysts with shell structure. Selectivity for MMA in the case of these catalysts is up to 97%. The space-time yield is described as 9.7 mol of MMA/(kg h) with a gold content in the catalyst of about 1% by weight. According to examples, an $NiO_x/Au$ catalyst shows much better activities and selectivities for MMA, while other combinations, for example Au with CuO or else $Co_3O_4$, are much less active and selective.

EP 2 177 267 also describes, in comparative example 7, a preparation of $Au/Co_3O_4$-containing catalysts proceeding from cobalt nitrate and auric acid by simultaneous application of Au and Co to an $SiO_2/MgO$ support. Experience has shown that this method of application leads to the best results for NiO/Au catalyst. But not in the case of use of cobalt, since the use of the resulting catalyst for preparation of MMA from methacrolein here achieves only 2.6% conversion and 45.8% selectivity at a space-time yield (STY) of 0.3 mol/(kg h). Comparative example 6 of the same patent describes the synthesis and use of an $Au/Fe_3O_4$ catalyst for the same conversion. This catalyst then achieves 10.4% conversion and 55.2% selectivity for MMA at an STY of 1.4 mol/(kg h). These catalysts are therefore not very suitable for industrial use.

EP 2 210 664 discloses a catalyst having, in the outer region, in the form of what is called an eggshell structure, nickel oxide and gold nanoparticles on a support composed of $SiO_2$, $Al_2O_3$ and a basic element, especially an alkali metal or alkaline earth metal. The nickel oxide is enriched at the surface, but is also present in lower concentrations in deeper layers of the catalyst particle. Such a catalyst exhibits very good activities and selectivities. However, the catalyst produced by the inventive preparation method from this application is relatively sensitive to abrasion and unstable, which is shown by a comparative example later on in the text. As a result, only relatively short service lives are available. The particular preparation method for production of the eggshell structure and the use of not uncritical nickel salts in the production of the catalyst place particular demands on industrial apparatus and the handling of fine nickel-containing dusts as inevitably occur in catalyst manufacture, for example in the process step of drying and calcining. Here too, the nickel doping component is described as necessary alongside gold nanoparticles and the particular anisotropic, inhomogeneous distribution of gold and dopant in order to achieve high activity and selectivity.

Xiaoyue Wan, Catalysis today, 233, 2014, p. 147 (Tab. 1) teaches that gold-based catalysts that have been applied to supports consisting of titanium dioxide would bring very poor or even zero yields coupled with extremely low selectivity in the oxidative esterification in a batchwise process.

C. Marsden, C. H. Christensen et al. in Green Chem., 2008, 10, 168-170 describe direct oxidative esterification (DOE for short) of various aldehydes in the presence of various catalysts comprising nanoparticulate gold on various supports. Acrolein is converted here to methyl acrylate over an Au/ZnO catalyst, but the reaction time at up to 40 hours for achievement of conversions of 90% is uneconomic for an industrial application, especially since only a selectivity of 87% is achieved. In continuation of these studies, McPherson et al. for Mintec likewise studied acrolein DOE to methyl acrylate with various nanoparticulate gold-containing catalysts (http://www.mintek.co.za/Mintek75/Proceedings/J04-McPherson.pdf). Here, Au catalysts supported on TiO2 are used in batchwise experiments, wherein it is likewise possible to achieve only 87% with extremely long reaction times at high conversions. At lower conversions, the selectivity is reported as much lower at 67% and is thus of no economic interest. On the basis of these results, application to a continuous process seemed uneconomic.

EP 1 393 800 in turn teaches that a gold-doped catalyst on a support composed of silica and titanium dioxide can bring about an acceptable yield, but is very unselective and produces large amounts of by-products. The corresponding catalyst had a titanium content below 5% by weight.

Corresponding relatively unsatisfactory results for $TiO_2$-doped supports of a gold- or gold/nickel oxide-based catalyst can be found in Ken Suzuki, ACS Catalysis., 3(8), 2013, p. 1845.

Moreover, all the systems, processes and catalysts described in the prior art do not describe, or only insufficiently describe, the formation of critical by-products, especially including hydrogenated by-products, which play an essential role in the isolation of market-standard qualities of alkyl methacrylates, especially MMA. Such a critical by-product which can be separated from MMA only with considerable apparatus complexity and considerable use of energy is methyl isobutyrate. These by-products are the corresponding saturated hydrocarbons of unsaturated compounds prepared in the process, for example the hydrogenated conversion products of the alkyl methacrylates, and usually have very similar boiling points or azeotropes, which makes distillative removal very complex and in some cases possible only with loss of yield.

This component occurs in very many standard industrial methyl methacrylate processes and is ultimately also found in the commercial MMA product as used, for example, for the production of PMMA, but in concentrations much less than 500 ppm, typically also less than 100 ppm. Overall, there is thus still a need to provide better catalysts for the oxidative esterification of aldehydes with alcohols, especially the preparation of MMA by direct oxidative esterification of methacrolein with methanol in the presence of oxygenous gas mixtures, having minimum generation of methyl isobutyrate which is difficult to remove. Thus, overall, there is a great interest in catalysts which lead to high yields with simultaneously high selectivities and long reactor on-stream times with simultaneously minimized generation of secondary components such as methyl isobutyrate that are removable from the monomer only with difficulty.

Standard catalysts for fulfilling the task, based on nickel-gold catalysts (EP 2177267 and EP2210664) and cobalt-gold catalysts (WO 2017084969), produce a pure product after workup having a methyl isobutyrate content in the range of 500-1000 ppm. It is sufficiently well-known from the literature that both nickel and cobalt are excellent hydrogenation catalysts (cf. Raney nickel and Raney cobalt from: Lehrbuch der Anorganischen Chemie [Inorganic Chemistry], Arnold Fr. Holleman, Egon Wiberg, Gruyter, ISBN: 9783110126419).

Overall, various catalysts are thus described in the prior art for direct oxidative esterification (DOE), for example for the conversion of unsaturated aldehydes such as acrolein and methacrolein. The raw materials, especially the unsaturated aldehyde compounds, are prepared in industrially practised processes. Acrolein is typically obtained by a gas phase partial oxidation with heterogeneous catalysts from propylene or propane.

Methacrolein can likewise be produced industrially by various routes. For example, methacrolein is prepared by a gas phase partial oxidation over a heterogeneous catalyst from a C-4 raw material, in the simplest case from isobutene, which is obtainable in turn from MTBE by elimination of methanol from MTBE (methyl tert-butyl ether). In a further process variant again, tert-butyl alcohol is used as C-4 raw material, which is introduced in gaseous form directly to the heterogeneous oxidation catalysts, optionally having been dehydrated in gaseous form over a preliminary catalyst. Isobutane is likewise useful and has been described as a raw material for the intermediate preparation of methacrolein. A good overview of the preparation of methacrolein by these C-4 process variants is given by the publication by Nagai and Ui, "Trends and Future of Monomer-MMA Technologies", Sumitomo Basic Chem. Research Lab. (http://www-.sumitomo-chem.co.jp/english/rd/report/theses/docs/20040200_30a.pdf)

Methacrolein can also be obtained from ethylene as C-2-based raw materials rather than from C-4-based starting materials. For this purpose, ethylene is first reacted with synthesis gas to give propanal. The latter affords, in a second stage, methacrolein together with formaldehyde. This approach can be read about, for example, in Ullmann's Encyclopedia of Industrial Chemistry 2012, Methacrylic Acid from Ethylene, and Trends and Future of Monomer-MMA Technologies, SUMITOMO KAGAKU 2004-II. Particular embodiments of the reaction can be read about, for example, in EP 0 092 097 or DE 28 55 504.

The resulting methacrolein is subsequently oxidized to methacrylic acid and finally esterified with an alkyl alcohol to give an alkyl methacrylate.

Overall, there is thus still a need to provide better catalysts for the oxidative esterification of aldehydes with alcohols. Furthermore, there is a great interest in catalysts which lead to high yields coupled with simultaneously high selectivities and long reactor on-stream times. The general technical teaching is that, in particular, titanium dioxide-supported and also titanium dioxide-doped supported catalysts are especially unsuitable for this purpose.

Problem to be Solved

The problem addressed by the present invention was primarily that of providing a novel process for synthesis of alkyl methacrylates, based on a novel catalyst, for a highly selective oxidative esterification of aldehydes to carboxylic esters. At the same time, this catalyst is to have high mechanical and chemical stability, especially in water- and carboxylic acid-containing mixtures, and is to have a better overall profile of activity, selectivity and lifetime under production conditions compared to the prior art.

A particular problem addressed was that this process is to be suitable for the oxidative esterification of methacrolein to an alkyl methacrylate, especially to MMA.

A particularly important partial aspect of the objective underlying the present invention was that of providing a novel process which, especially in the conversion of aldehydes to carboxylic esters, leads to reduced formation of by-products and hence to a higher selectivity. By-products of this kind are, for example, methacrylic acid or else alkyl alkoxyisobutyrate, in the case of the MMA synthesis methyl methoxyisobutyrate (MMIB).

A particularly important partial aspect of the objective underlying the present invention was that of providing a novel process which, especially in the conversion of aldehydes to carboxylic esters, leads to reduced formation of by-products, especially hydrogenated by-products, and hence to a higher product purity. What is being sought is thus, more particularly, a catalyst that executes hydrogenation of the end products only to a limited degree, if at all.

Further problems which are not stated explicitly may become apparent from the description, the examples, the claims or the overall context of the present invention.

SUMMARY OF THE INVENTION

The stated objects have been achieved with the aid of a novel process for the oxidative esterification of aldehydes to carboxylic esters, in which entirely novel catalyst particles that are surprisingly efficient and long-lived with regard to the teaching of the prior art are used for the process. Preferably, the process is an oxidative esterification of an aldehyde in the presence of oxygen and an alcohol to give a carboxylic ester. The process according to the invention may more preferably be a process for the oxidative esterification of methacrolein in the presence of oxygenous gases and an alcohol to give an alkyl methacrylate, especially of methacrolein in the presence of methanol to give MMA.

Alternatively, in the case of this use, it is also possible to react methacrolein with oxygen and a di-, tri- or tetrafunctional alcohol to give a hydroxyalkyl methacrylate and di-, tri- or tetramethacrylate. The latter compounds are known as crosslinkers. A particularly preferred example of a difunctional alcohol is ethylene glycol.

DETAILED DESCRIPTION OF THE INVENTION

Figure 1:
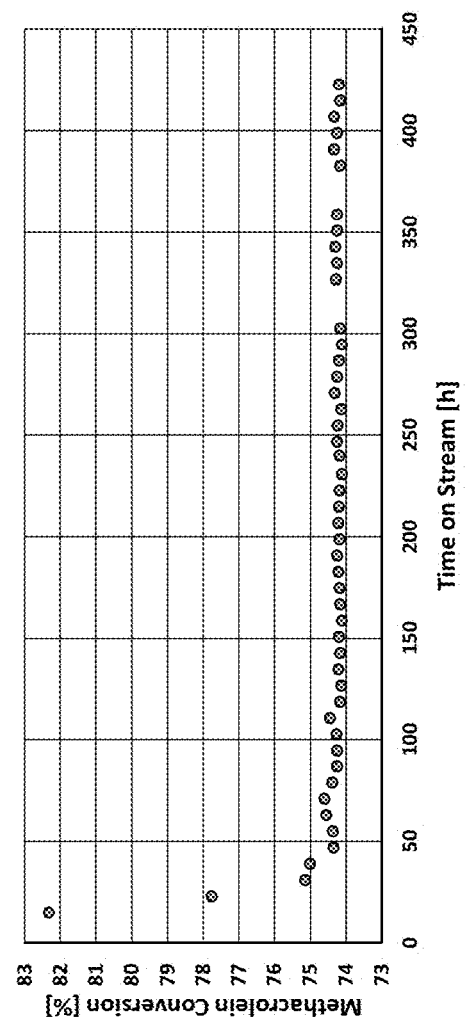
FIG. 1 shows, for Table 4, the methacrolein conversion as a function of the run time in continuous operation. It is thus especially possible to demonstrate the long-term activity of the catalyst.

A novel process for oxidative esterification of aldehydes to carboxylic esters is described. Novel catalyst particles that are surprisingly efficient and long-lived with regard to the teaching of the prior art are used in the process. The process is preferably an oxidative esterification of an aldehyde in the presence of oxygen and an alcohol to give a carboxylic ester. The process is more preferably a process for oxidative esterification of methacrolein in the presence of oxygenous gases and an alcohol to give an alkyl methacrylate, especially of methacrolein in the presence of methanol to give MMA.

Alternatively, it is possible to react methacrolein with oxygen and a di-, tri- or tetrafunctional alcohol to give a hydroxyalkyl methacrylate and di-, tri- or tetramethacrylate. The di-, tri-, and tetrafunctional alcohols are known as crosslinkers. A particularly preferred example of a difunctional alcohol is ethylene glycol.

The catalysts used in the process in accordance with the invention are characterized in that the catalyst particle consists of 0.1% to 3% by weight, preferably 0.3% to 2.5% by weight, of gold, 25% to 99.8% by weight, preferably 50% to 99.5% by weight, of $TiO_2$, 0% to 50% by weight, preferably 0% to 20% by weight, of silicon oxides, 0% to 25% by weight of $Al_2O_3$, 0% to 25% by weight of oxides of alkali metals, alkaline earth metals, rare earth metals and/or zirconium, 0% to 20% by weight, preferably 0% to 10% by weight, of iron oxides, zinc oxides, nickel oxides and/or cobalt oxides and 0% to 5% by weight of further components. In general, the gold is in elemental form in the form of Au{0} and in the form of nanoparticles, while all other components in the catalyst particle are in oxidic form.

In addition, it is a feature of these catalyst particles used in the process in accordance with the invention that the gold, optionally together with iron oxides, zinc oxides, nickel oxides and/or cobalt oxides, is present in the form of particles—also referred to as primary particles—having an average diameter between 2 and 10 nm and these particles are bound to the surface of the rest of the catalyst particle.

In the case of mixed phases of gold with the oxides mentioned, however, this does not necessarily mean that these oxides must entirely be some of the particles having an average diameter between 2 and 10 nm in the catalyst particle. Instead, some of the oxides may also be part of the support material and, for example, be bound in another way in some other form, particularly to the surface of the support material. More preferably, however, the catalyst particle does not include any iron oxide, zinc oxide, nickel oxide and/or cobalt oxide, but has exclusively gold as the sole active component. The catalyst particle used in the process in accordance with the invention has an average geometric equivalent diameter between 5 μm and 10 mm, preferably between 10 μm and 10 mm, more preferably between 200 μm and 5 mm.

According to the production method, it is possible that the gold is present either in the form of pure particles or in a mixed form, for example with one of the oxides mentioned, for example cobalt oxide. In this latter case, the gold is generally mixed only with a portion of the oxide. In addition, it is optionally also possible in both embodiments that the gold or gold-containing particles, for stabilization, are additionally provided with a thin layer, for example of $TiO_2$, $SiO_2$ and/or $Al_2O_3$.

Furthermore, the process according to the invention is conducted continuously, by means of heterogeneous catalysis in a liquid phase. Preferably, in the continuously operated reactor, there is a triphasic system with a solid catalyst phase, a liquid reaction phase and a gas phase.

In a particular embodiment of the present invention, the process is characterized in that the catalyst particle is composed predominantly or even exclusively of gold and $TiO_2$. In this variant, the catalyst particle consists preferably of 0.3% to 2.5% by weight of gold, 96% to 99.5% by weight of $TiO_2$ and not more than 3.7% by weight, more preferably 1.5% by weight, of further components which are neither gold nor $TiO_2$.

Preferably, the catalyst particles used in accordance with the invention are porous. In this case, the porosity generally does not relate to the gold or gold-containing phases. Such porous catalyst particles have a specific surface area between 20 and 300 $m^2/g$, preferably between 30 and 200 $m^2/g$, more preferably between 80 and 150 $m^2/g$. In addition, the average pore diameter is generally 2 to 50 nm, preferably 5 to 30 nm, more preferably 10 to 25 nm.

An optional component of the catalyst particle used in accordance with the invention is what are called basic elements. These basic elements are especially alkali metals (Li, Na, K, Rb, Cs, Fr), alkaline earth metals (Be, Mg, Ca, Sr, Ba), rare earth metals (Sc, Y, La, Ce, Pr, Nd, Pm, Sm, Eu, Gd, Tb, Dy, Ho, Er, Tm, Yb, Lu) or mixtures of these metals. The basic element is generally also present in oxide form. It is entirely possible in the case of prolonged operation of the process with the catalyst particles used in accordance with the invention that a freshly prepared catalyst can lose a portion of the basic element during a process for preparing carboxylic esters. According to the nature of the catalyst, this may lead either to a slight improvement or to a deterioration in the activity and/or selectivity of the process, and is caused by acids formed as by-product during the process.

Further suitable metal oxides, especially for the support component of the catalyst, are zirconium oxides.

The further components that are optionally present in the catalyst particle at up to 5% by weight are components that first of all differ from the other compounds or elements listed. An especially suitable example of such a further component is zirconium, or a zirconium compound, such as zirconium oxide in particular.

In a preferred embodiment of the present invention, the gold-containing primary particles are in the outer region of the catalyst particle. In a second, likewise preferred embodiment, these primary particles are distributed homogeneously across the catalyst particle.

In the first embodiment mentioned, the catalyst particles used in the process in accordance with the invention are characterized in that the maximum gold concentration or the maximum iron, zinc or cobalt concentration of the catalyst particle is to be found in the outer region thereof. Said outer region makes up a maximum of 60%, preferably a maximum of 40% and more preferably a maximum of 30% of the geometric equivalent diameter of the catalyst particle. In this context, the gold concentration or iron, zinc and/or cobalt concentration in this outer region is at least 1.5 times, preferably at least twice and especially preferably at least 2.5 times as high as the corresponding concentration of these elements in the middle region which makes up the remaining region of the geometric equivalent diameter of the catalyst particle. More preferably, the gold in this embodiment is present to an extent of more than 90% in this outer region. Such a construction of the catalyst particle is referred to as an eggshell structure.

The determination and analysis of the distribution of the concentrations of gold and/or iron, nickel, zinc and/or cobalt across the catalyst particle profile can be effected, for example, by the embedding of the particles into a polymer matrix, subsequent polishing and then SEM-EDX analysis. An analogous analysis method by means of x-ray microanalysis (EPMA) is described, for example, in EP 2 210 664 A1 on page 18.

The catalyst particles used in accordance with the invention and hence the process according to the invention, particularly with regard to the prior art discussed above, are notable for a number of advantages that were not to be expected beforehand. For instance, these catalyst particles are especially notable for the retention of a high activity with simultaneously high selectivity of the catalyst particle used for the oxidative esterification over a long period. Thus, the catalyst particles used in accordance with the invention have a particularly good combination of a) low mechanical abrasion of the catalyst particle, b) low leaching of metal ions, which can lead to problems with regard to stability, for example, in the case of iron in an MMA prepared in accordance with the invention, out of the particle and c) long-term retention of catalyst performance with regard to activity and selectivity.

Particularly surprisingly, it has been found that the catalysts according to the invention lead not only to a generally higher selectivity but that the formation of particularly unwanted by-products in particular, for example of methacrylic acid. In the same way, for example, in the case of the oxidative esterification of methacrolein with methanol to give MMA, a further reduction in formation of methyl methoxyisobutyrate (MMIB) was found.

Furthermore, it has been found that, surprisingly, the catalysts used in accordance with the invention distinctly reduced the formation of hydrogenated by-products of the desired main products compared to the prior art. Thus, in accordance with the invention, the formation of, for example, hydrogenated MMA in the case of use of a $TiO_2$-based catalyst according to the invention, by comparison with the best catalysts described in the prior art, is reduced by a factor of 10 from a content between 500 and 1000 ppm to a content between 50 and 100 ppm.

Many of the by-products of the reaction are formed especially at high concentrations of the starting materials. Dimeric methacrolein and the esters thereof, for example, form preferentially at high concentrations of the methacrolein starting material. Dimethoxyisobutene forms especially under neutral and acidic conditions at high concentrations of methanol and methacrolein. Methyl 3-methoxyisobutyrate (3-MMIB for short) forms at high concentrations of methanol as a Michael addition product with methacrolein (and subsequent direct oxidative esterification), particularly under neutral and basic conditions.

The formation of dimeric methacroleins (MAL dimer for short) can be counteracted at relatively high pH values in such a way that the conversion of the MAL is higher at high pH values and the concentration of the same is thus lower. This results in reduced formation of the MAL dimer or esters thereof. However, according to the prior art, the change in the pH, on the other hand, would increase the preferential formation of the other by-product, 3-MMIB. According to the invention, however, the formation of the MAL dimer plays a surprisingly minor role, and so it now becomes possible to improve the yield and selectivity of the process, surprisingly, with rising conversion. This is effected in such a way that an additional surprising effect in accordance with the invention is that the process can be operated at particularly high conversion without needing to extend the residence time in the reactor.

The Diels-Alder reaction which leads to formation of dimeric MAL or ester thereof is especially also promoted by a higher temperature. According to the invention, this can surprisingly be additionally counteracted by more moderate reaction conditions.

Equally surprisingly, the formation of a methyl isobutyrate from secondary hydrogenation reaction is also distinctly reduced, such that the catalyst present, in a continuous process, after a run-in period, retains a surprisingly high selectivity at a constant level over a very long operating period.

Preferably, the catalyst particles have an average geometric equivalent diameter between 10 µm, preferably 100 µm, and 5 mm, more preferably between 500 µm and 2 mm. The diameter here is based on the average geometric equivalent diameter (also referred to synonymously hereinafter as average equivalent diameter or geometric equivalent diameter) in the form of a volume-equivalent sphere diameter. The average equivalent diameter of such an inhomogeneous body can be determined in that the average equivalent diameter corresponds to the diameter $d_v$ of a sphere of equal volume to the inhomogeneous body. For this purpose, first of all—neglecting the porosity—the volume of the catalyst particle is determined. This can be effected in the case of simple, homogeneous bodies, for example regularly shaped cylinders, by simply measuring a microscopic absorption, for example. In the case of ideally spherical particles, the determination can even be dispensed with entirely, since the result corresponds to the actual ball diameter.

In the case of very inhomogeneously shaped particles, the volume is determined and—if this is done in a porosity-dependent manner—the result is corrected by the porosity to be determined additionally.

The formula for calculation of the average equivalent diameter, which, in accordance with the invention, is more specifically the volume-equivalent sphere diameter $d_v$, depending on the volume V is:

$$d_v = \sqrt[3]{\frac{6*V}{\pi}}$$

In the case that the gold-containing particles are present close to the surface of the catalyst particle, the active outer region of such a catalyst particle with eggshell structure is referred to hereinafter as outer region. The thickness of this outer region is preferably between 2 and 100 µm, preferably between 5 and 50 µm. The size of the geometric equivalent diameter is stated because the particles need not necessarily be in entirely spherical form, but may quite possibly also have more complex forms.

It should also be pointed out that the boundary thus contemplated between the core and a shell in the case of such an optional eggshell structure, moreover, will not be sharp, but may especially be in the form of a gradient with varying composition. For example, the concentration of gold nanoparticles, viewed from the core, may thus increase from the inside outward. This arises merely from the fact that the particles of the invention generally have porosity. In the ideal case, an illustrative value of thickness 80 µm of the outer region, for example in the case of a particle having an equivalent diameter of 200 µm, means that, viewed over the diameter, at either outer end thereof, there is 40 µm of outer region with 120 µm of middle region in between. This size was chosen in order to describe the eggshell structure of the catalyst of the invention. The boundary between the outer and inner region can be chosen relatively freely by the person skilled in the art within the ranges specified in the examination of the particles. What is crucial in accordance with the invention is that there is a boundary within the range specified where the conditions exist with regard to the iron, zinc, nickel and/or cobalt concentration and the gold concentration. In relation to the iron, zinc and especially the cobalt concentration, this is the inventive core of the present invention.

The parameters of a particularly preferred embodiment of the present invention are described hereinafter. Given compliance with the settings specified here, particularly good results of the process are obtained in relation to yield and selectivity over a long period of operation. However, this is not supposed to mean that there are not alternative settings of the present invention that lead to similar results. Instead, it should be pointed out that the catalyst used in accordance with the invention brings surprisingly good results compared to the prior art over a broad range.

More particularly, it is a feature of the process in this particularly preferred embodiment that the reaction between methacrolein and an alkyl alcohol, especially methanol, is conducted continuously in the presence of an oxygenous gas observing the following parameters:

I. at a reaction temperature between 40-120° C., more preferably between 50 and 100° C.,
II. at an absolute pressure between 1 and 20 bar, more preferably between 2 and 15 bar,
III. with a slurry density of the catalyst, especially particulate catalyst, which is being stirred and swirled in the steady-state product mixture comprising MMA, methacrolein, methanol and water, between 1% and 20% by weight, more preferably between 2% and 15% by weight.

Preferably, the methacrolein reactant is not completely converted in at least one reactor in each case. Instead, preferably after partial conversion between 20% and 95%, it is separated continuously from the catalyst by means of filtration and sent to the workup. In the workup, the remaining methacrolein can then, for example, be isolated and recycled into the reaction as reactant.

The process can surprisingly be configured in a particularly economically viable manner when the molar excess of methanol to methacrolein fed continuously to the reactor is limited to 1:1 to 15:1. The concept of "continuous feeding" here describes a period of time appropriate for the reaction, irrespective of whether methacrolein and methanol are added simultaneously or sequentially. Both methacrolein and methanol are only partly converted using the novel catalyst systems in the process which is likewise according to the invention. This means that the resulting reaction mixture, after separation from the catalyst particle, is purified in such a way that unconverted methacrolein and methanol are separated from the product esters and fed back to the reaction.

More preferably, air is fed continuously to the reactor as oxygenous gas. Likewise more preferably, the oxygen content of the gas phase which is present and forms above the reaction mixture is between 2% and 8% by volume.

In a very particular variant of the reaction, the methacrolein reactant is reacted with the alkyl alcohol in multiple reactors connected in series. In this case too, it is especially preferable not to achieve full conversion, but instead, after a partial conversion between 20% and 90%, especially preferably between 40% and 80%, to continuously separate the methacrolein from the catalyst by means of filtration and feed it to the workup.

In a likewise preferred, alternative variant of the reaction, the methacrolein reactant is reacted with the alkyl alcohol in exactly one reactor. In this case too, it is especially preferable not to achieve full conversion, but instead, after a partial conversion between 20% and 90%, especially preferably between 40% and 80%, to continuously separate the methacrolein from the catalyst by means of filtration and feed it to the workup.

The oxidative esterification according to the invention is conducted continuously in the presence of the catalyst particle. More preferably, the catalyst is employed in suspension form (as a slurry) in a stirred reactor during the oxidative esterification.

EXAMPLES

Example 1

Preparation of a Catalyst with 1.4% by Weight of Au on $TiO_2$ Support (d50=20 μm)

In a glass flask with mechanical stirring, 1.82 g of auric acid ($HAuCl_4*3H_2O$) are dissolved in 600 g of water and heated to internal temperature 70° C. The pH of the solution thus obtained is about 2.2 and is adjusted to 7.5 with 0.5 M $Na_2CO_3$ solution over a period of 10 minutes. Subsequently, 50 g of $TiO_2$ support (product name: Aeroperl P25, Evonik Industries, prepared from $TiCl_4$ by flame pyrolysis, grain size d50=20 μm, 75% anatase, 25% rutile) are directly added all at once while stirring (400 rpm). The suspension thus obtained is stirred at 70° C. for 60 min, keeping the pH constant at 7.5. The pH rises into the basic range during this period and is kept at 7.5 with 2.0 M $HNO_3$ solution and 0.5 M $Na_2CO_3$ solution. The suspension is centrifuged while hot and decanted, and the residue is converted to a slurry again and centrifuged again a total of five times with 250 ml of distilled water each time (5 ml of dist. water/g of support). The residual conductivity of the wash water obtained is to be below 100 μS/cm². The catalyst obtained is dried in a thin layer at 120° C. for 16 h. The catalyst is heated to 70° C. under nitrogen and then reduced with a stream of 5% by volume of $H_2$ in $N_2$ and cooled down to room temperature, and the gas stream is ended. The performance of the catalyst was evaluated in a batch test (see Table 1).

Example 2

Preparation of a Catalyst with 1.4% by Weight of Au on $TiO_2$ Support (d50=40 μm)

In a glass flask with mechanical stirring, 1.82 g of auric acid ($HAuCl_4*3H_2O$) are dissolved in 600 g of water and heated to internal temperature 70° C. The pH of the solution thus obtained is about 2.2 and is adjusted to 7.5 with 0.5 M $Na_2CO_3$ solution and then maintained over a period of 10 minutes. Subsequently, 50 g of $TiO_2$ support (TP Hombikat, Huntsman, d50=about 40 μm—development product as stationary phase of HPLC columns, 95% anatase structure) are added all at once while stirring (400 rpm). The suspension thus obtained is stirred at 70° C. for 60 min, keeping the pH constant at 7.5. The pH rises into the basic range during this period and is kept at 7.5 with 2.0 M $HNO_3$ solution and 0.5 M $Na_2CO_3$ solution. the suspension is vacuum-filtered while still hot through a suction filter and washed 5 times with 250 ml of dist. water each time (5 ml of dist. water/g of support). The residual conductivity of the wash water obtained is to be below 100 μS/cm². The catalyst obtained is dried in a thin layer at 120° C. for 16 h. The catalyst is heated to 70° C. under nitrogen and then reduced with a stream of 5% by volume of $H_2$ in $N_2$ and cooled down to room temperature, and the gas stream is ended. The performance of the catalyst was evaluated in a batch test and continuously [see Table 1 (batch test) and Table 2 (continuous)].

Example 3

Preparation of a Catalyst with 1.1% by Weight of Au on $TiO_2$ Support (d50=30 μm)

In a glass flask with mechanical stirring, 1.82 g of auric acid ($HAuCl_4*3H_2O$) are dissolved in 600 g of water and heated to internal temperature 70° C. The pH of the solution thus obtained is about 2.2 and is adjusted to 7.5 with 0.5 M $Na_2CO_3$ solution and then maintained over a period of 10 minutes. Subsequently, 50 g of $TiO_2$ support (product name: Aeroperl P25 H6, Evonik Industries, P25 recalcined at 600° C. under $N_2$ atmosphere, grain size d50=30 μm) were added all at once while stirring (400 rpm). The suspension thus obtained is stirred at 70° C. for 60 min, keeping the pH constant at 7.5. The pH rises into the basic range during this period and is kept at 7.5 with 2.0 M $HNO_3$ solution and 0.5 M $Na_2CO_3$ solution. The suspension is centrifuged while hot and decanted, and the residue is converted to a slurry again and centrifuged again a total of five times with 250 ml of distilled water each time (5 ml of dist. water/g of support). The residual conductivity of the wash water obtained is to be below 100 μS/cm². The catalyst obtained is dried in a thin layer at 120° C. for 16 h. The catalyst is heated to 70° C. under nitrogen and then reduced with a stream of 5% by volume of $H_2$ in $N_2$ and cooled down to RT, and the gas stream is ended. The performance of the catalyst was evaluated in a batch test (see Table 1).

Example 4

Preparation of a Catalyst with 1.0% by Weight of Au on $TiO_2$ Support (2×5 mm)

In a glass flask with mechanical stirring, 1.32 g of auric acid ($HAuCl_4*3H_2O$) are dissolved in 600 g of water and heated to internal temperature 70° C. The pH of the solution thus obtained is about 2.5 and is adjusted to 7.5 with 0.5 M $Na_2CO_3$ solution and then maintained over a period of 10 minutes. Subsequently, 50 g of $TiO_2$ support (Aeroperl P25 with binder extruded to 2×5 mm rods and calcined, Evonik Industries) were added all at once while stirring (400 rpm). The suspension thus obtained is stirred at 70° C. for 60 min, keeping the pH constant at 7.5. The pH rises into the basic range during this period and is kept at 7.5 with 2.0 M $HNO_3$ solution and 0.5 M $Na_2CO_3$ solution. The catalyst rods are filtered off with suction while still hot and washed with dist. water until the residual conductivity of the wash water obtained was below 100 μS/cm². The catalyst obtained is dried in a thin layer at 120° C. for 16 h. The catalyst is heated to 70° C. under nitrogen with gentle circulation (6 rpm) and then reduced with a stream of 5% by volume of $H_2$ in $N_2$ and cooled down to room temperature, and the gas stream is ended.

Example 5

Preparation of a Catalyst with 1.0% by Weight of Au on $TiO_2$ Support (37-100 μm)

The catalyst from Example 4 was comminuted in an agate mortar and the fraction <100 μm was sieved off using a wire mesh sieve. The residue was comminuted again in a mortar and the procedure was repeated until all the material had been comminuted to a size <100 μm. The residue thus obtained was freed of the fines fraction using a sieve having a mesh size of 37 μm. The catalyst with a grain size of 37-100 μm remaining on the sieve is the catalyst for Example 5 in Table 1 of the batch test and Example 2 in Table 2 of the continuous test.

Example 6

Preparation of a Catalyst with 1.0% by Weight of Au on $TiO_2$ Support (<37 μm)

The catalyst from Example 4 was comminuted in an agate mortar and the fraction <100 μm was sieved off using a wire mesh sieve. The residue was comminuted again in a mortar and the procedure was repeated until all the material had been comminuted to a size <100 μm. The residue thus obtained was freed of the coarse fraction using a sieve having a mesh size of 37 μm. The catalyst that passes through the sieve with a grain size of <37 μm is the catalyst for Example 6 in Table 1.

Example 7

Preparation of an Uncalcined Catalyst with 1.4% by Weight of Au on $TiO_2$ Support In a glass flask with mechanical stirring, 1.82 g of auric acid ($HAuCl_4*3H_2O$) are dissolved in 600 g of water and heated to internal temperature 70° C. The pH of the solution thus obtained is about 2.2 and is adjusted to 7.5 with 0.5 M $Na_2CO_3$ solution and then maintained over a period of 10 minutes. Subsequently, 50 g of $TiO_2$ support (product name: Aeroperl P25, Evonik Industries, prepared from $TiCl_4$ by flame pyrolysis, grain size d50=20 μm, 75% anatase, 25% rutile) are added all at once while stirring (400 rpm). The suspension thus obtained is stirred at 70° C. for 60 min, keeping the pH constant at 7.5. The pH rises into the basic range during this period and is kept at 7.5 with 2.0 M $HNO_3$ solution and 0.5 M $Na_2CO_3$ solution. The suspension is centrifuged while hot and decanted, and the residue is converted to a slurry again and centrifuged again a total of five times with 250 ml of distilled water each time (5 ml of dist. water/g of support). The residual conductivity of the wash water obtained is to be below 100 μS/cm². The catalyst obtained is dried in a thin layer at 120° C. for 16 h. The performance of the catalyst thus obtained was evaluated in a batch test (see Table 1).

Example 8

Preparation of a Catalyst with 1.4% by Weight of Au on $TiO_2$ Support (Calcined for 3 h)

In a glass flask with mechanical stirring, 1.82 g of auric acid ($HAuCl_4*3H_2O$) are dissolved in 600 g of water and heated to internal temperature 70° C. The pH of the solution thus obtained is about 2.2 and is adjusted to 7.5 with 0.5 M $Na_2CO_3$ solution and then maintained over a period of 10 minutes. Subsequently, 50 g of $TiO_2$ support (product name: Aeroperl P25, Evonik Industries, prepared from $TiCl_4$ by flame pyrolysis, grain size d50=20 μm, 75% anatase, 25% rutile) are added all at once while stirring (400 rpm). The suspension thus obtained is stirred at 70° C. for 60 min, keeping the pH constant at 7.5. The pH rises into the basic range during this period and is kept at 7.5 with 2.0 M $HNO_3$ solution and 0.5 M $Na_2CO_3$ solution. The suspension is centrifuged while hot and decanted, and the residue is converted to a slurry again and centrifuged again a total of five times with 250 ml of distilled water each time (5 ml of dist. water/g of support). The residual conductivity of the wash water obtained is to be below 100 μS/cm². The catalyst obtained is dried in a thin layer at 120° C. for 16 h. The catalyst is heated to 70° C. under nitrogen and then reduced with a stream of 5% by volume of $H_2$ in $N_2$ for 3 h and cooled down to room temperature, and the gas stream is ended. The performance of the catalyst was evaluated in a batch test (see Table 1).

Example 9

Preparation of a Catalyst with 1.4% by Weight of Au on $TiO_2$ Support (Calcined for 4.5 h)

In a glass flask with mechanical stirring, 1.82 g of auric acid ($HAuCl_4*3H_2O$) are dissolved in 600 g of water and heated to internal temperature 70° C. The pH of the solution thus obtained is about 2.2 and is adjusted to 7.5 with 0.5 M $Na_2CO_3$ solution and then maintained over a period of 10 minutes. Subsequently, 50 g of $TiO_2$ support (product name: Aeroperl P25, Evonik Industries, prepared from $TiCl_4$ by flame pyrolysis, grain size d50=20 μm, 75% anatase, 25% rutile) are added all at once while stirring (400 rpm). The suspension thus obtained is stirred at 70° C. for 60 min, keeping the pH constant at 7.5. The pH rises into the basic range during this period and is kept at 7.5 with 2.0 M $HNO_3$ solution and 0.5 M $Na_2CO_3$ solution. The suspension is centrifuged while hot and decanted, and the residue is converted to a slurry again and centrifuged again a total of five times with 250 ml of distilled water each time (5 ml of dist. water/g of support). The residual conductivity of the wash water obtained is to be below 100 μS/cm². The catalyst obtained is dried in a thin layer at 120° C. for 16 h. The catalyst is heated to 70° C. under nitrogen and then reduced with a stream of 5% by volume of $H_2$ in $N_2$ for 4.5 h and cooled down to room temperature, and the gas stream is ended. The performance of the catalyst was evaluated in a batch test (see Table 1).

Example 10

Preparation of a Catalyst with 1.4% by Weight of Au on $TiO_2$ Support (Formate, Reduced)

In a glass flask with mechanical stirring, 1.82 g of auric acid ($HAuCl_4*3H_2O$) are dissolved in 600 g of water and heated to internal temperature 70° C. The pH of the solution thus obtained is about 2.2 and is adjusted to 7.5 with 0.5 M $Na_2CO_3$ solution and then maintained over a period of 10 minutes. Subsequently, 50 g of $TiO_2$ support (TP Hombikat, Huntsman, d50=about 40 μm—development product as stationary phase of HPLC columns, 95% anatase structure) are added all at once while stirring (400 rpm). The suspension thus obtained is stirred at 70° C. for 60 min, keeping the pH constant at 7.5. The pH rises into the basic range during this period and is kept at 7.5 with 2.0 M $HNO_3$ solution and 0.5 M $Na_2CO_3$ solution. the suspension is vacuum-filtered while still hot through a suction filter and washed 5 times with 250 ml of dist. water each time (5 ml of dist. water/g of support). The residual conductivity of the wash water obtained is to be below 100 μS/cm². The catalyst obtained is dried in a thin layer at 120° C. for 16 h and then stirred in a 2% by weight solution of sodium formate in methanol at 70° C. for 4 h, filtered, washed to neutral pH and dried again in a thin layer at 120° C. for 16 h. The performance of the catalyst thus obtained was evaluated in a batch test (see Table 1).

Example 11

Preparation of a Catalyst with 1.4% by Weight of Au on $TiO_2$ Support (Formate, Reduced in Water)

In a glass flask with mechanical stirring, 1.82 g of auric acid ($HAuCl_4*3H_2O$) are dissolved in 600 g of water and heated to internal temperature 70° C. The pH of the solution thus obtained is about 2.2 and is adjusted to 7.5 with 0.5 M $Na_2CO_3$ solution and then maintained over a period of 10 minutes. Subsequently, 50 g of $TiO_2$ support (TP Hombikat, Huntsman, d50=about 40 μm—development product as stationary phase of HPLC columns, 95% anatase structure) are added all at once while stirring (400 rpm). The suspension thus obtained is stirred at 70° C. for 60 min, keeping the pH constant at 7.5. The pH rises into the basic range during this period and is kept at 7.5 with 2.0 M $HNO_3$ solution and 0.5 M $Na_2CO_3$ solution. The suspension is vacuum-filtered while still hot through a suction filter and washed 5 times with 250 ml of dist. water each time (5 ml of dist. water/g of support). The residual conductivity of the wash water obtained is to be below 100 μS/cm². The catalyst obtained is dried in a thin layer at 120° C. for 16 h and then stirred in a 2% by weight solution of sodium formate in water at 70° C. for 4 h, filtered, washed to neutral pH and dried again in a thin layer at 120° C. for 16 h. The performance of the catalyst thus obtained was evaluated in a batch test (see Table 1).

Example 12

Preparation of a Catalyst with 1.4% by Weight of Au on $TiO_2$ Support (Methanol, Reduced with $O_2$)

In a glass flask with mechanical stirring, 1.82 g of auric acid ($HAuCl_4*3H_2O$) are dissolved in 600 g of water and heated to internal temperature 70° C. The pH of the solution thus obtained is about 2.2 and is adjusted to 7.5 with 0.5 M $Na_2CO_3$ solution and then maintained over a period of 10 minutes. Subsequently, 50 g of $TiO_2$ support (TP Hombikat, Huntsman, d50=about 40 μm—development product as stationary phase of HPLC columns, 95% anatase structure) are added all at once while stirring (400 rpm). The suspension thus obtained is stirred at 70° C. for 60 min, keeping the pH constant at 7.5. The pH rises into the basic range during this period and is kept at 7.5 with 2.0 M $HNO_3$ solution and 0.5 M $Na_2CO_3$ solution. The suspension is vacuum-filtered while still hot through a suction filter and washed 5 times with 250 ml of dist. water each time (5 ml of dist. water/g of support). The residual conductivity of the wash water obtained is to be below 100 μS/cm². The catalyst obtained is dried in a thin layer at 120° C., then stirred in methanol and sparged with oxygen for one hour, then filtered, washed to neutral pH and dried again in a thin layer at 120° C. for 16 h. The performance of the catalyst thus obtained was evaluated in a batch test (see Table 1).

Example 13

Preparation of a Catalyst with 1.4% by Weight of Au on $TiO_2$ Support (Methanol, Reduced with $N_2$)

In a glass flask with mechanical stirring, 1.82 g of auric acid ($HAuCl_4*3H_2O$) are dissolved in 600 g of water and heated to internal temperature 70° C. The pH of the solution thus obtained is about 2.2 and is adjusted to 7.5 with 0.5 M $Na_2CO_3$ solution and then maintained over a period of 10 minutes. Subsequently, 50 g of $TiO_2$ support (TP Hombikat, Huntsman, d50=about 40 μm—development product as stationary phase of HPLC columns, 95% anatase structure) are added all at once while stirring (400 rpm). The suspension thus obtained is stirred at 70° C. for 60 min, keeping the pH constant at 7.5. The pH rises into the basic range during this period and is kept at 7.5 with 2.0 M $HNO_3$ solution and 0.5 M $Na_2CO_3$ solution. The suspension is vacuum-filtered while still hot through a suction filter and washed 5 times with 250 ml of dist. water each time (5 ml of dist. water/g of support). The residual conductivity of the wash water obtained is to be below 100 μS/cm². The catalyst obtained is dried in a thin layer at 120° C. for 16 h, then stirred in methanol and left under a nitrogen atmosphere during this time, then filtered, washed to neutral pH and dried again in a thin layer at 120° C. for 16 h. The performance of the catalyst thus obtained was evaluated in a batch test (see Table 1).

Example 14

Preparation of a Catalyst with 0.7% by Weight of Au on $TiO_2$ Support (d50=40 μm)

In a glass flask with mechanical stirring, 0.92 g of auric acid ($HAuCl_4*3H_2O$) are dissolved in 600 g of water and heated to internal temperature 70° C. The pH of the solution thus obtained is about 2.2 and is adjusted to 7.5 with 0.5 M $Na_2CO_3$ solution and then maintained over a period of 10 minutes. Subsequently, 50 g of $TiO_2$ support (TP Hombikat, Huntsman, d50=about 40 μm—development product as stationary phase of HPLC columns, 95% anatase structure) are added all at once while stirring (400 rpm). The suspension thus obtained is stirred at 70° C. for 60 min, keeping the pH constant at 7.5. The pH rises into the basic range during this period and is kept at 7.5 with 2.0 M $HNO_3$ solution and 0.5 M $Na_2CO_3$ solution. The suspension is vacuum-filtered while still hot through a suction filter and washed 5 times with 250 ml of dist. water each time (5 ml of dist. water/g of support). The residual conductivity of the wash water obtained is to be below 100 μS/cm². The catalyst obtained is dried in a thin layer at 120° C. for 16 h. The catalyst is heated to 70° C. under nitrogen and then reduced with a stream of 5% by volume of $H_2$ in $N_2$ and cooled down to RT, and the gas stream is ended. The performance of the catalyst was evaluated in a batch test [see Table 1 (batch test)].

Example 15

Preparation of a Catalyst with 0.13% by Weight of Au on $TiO_2$ Support (d50=40 μm)

In a glass flask with mechanical stirring, 0.19 g of auric acid ($HAuCl_4*3H_2O$) are dissolved in 600 g of water and heated to internal temperature 70° C. The pH of the solution thus obtained is about 2.2 and is adjusted to 7.5 with 0.5 M $Na_2CO_3$ solution and then maintained over a period of 10 minutes. Subsequently, 50 g of $TiO_2$ support (TP Hombikat, Huntsman, d50=about 40 μm—development product as stationary phase of HPLC columns, 95% anatase structure) are added all at once while stirring (400 rpm). The suspension thus obtained is stirred at 70° C. for 60 min, keeping the pH constant at 7.5. The pH rises into the basic range during this period and is kept at 7.5 with 2.0 M $HNO_3$ solution and 0.5 M $Na_2CO_3$ solution. The suspension is vacuum-filtered while still hot through a suction filter and washed 5 times with 250 ml of dist. water each time (5 ml of dist. water/g of support). The residual conductivity of the wash water obtained is to be below 100 µS/cm². The catalyst obtained is dried in a thin layer at 120° C. for 16 h. The catalyst is heated to 70° C. under nitrogen and then reduced with a stream of 5% by volume of $H_2$ in $N_2$ and cooled down to room temperature, and the gas stream is ended. The performance of the catalyst was evaluated in a batch test [see Table 1 (batch test)].

Example 16

Preparation of an Au Catalyst on $TiO_2/ZrO_2$ Support

In a glass flask with mechanical stirring, 1.82 g of auric acid ($HAuCl_4*3H_2O$) are dissolved in 600 g of water and heated to internal temperature 70° C. The pH of the solution thus obtained is about 2.2 and is adjusted to 7.5 with 0.5 M $Na_2CO_3$ solution and then maintained over a period of 10 minutes. Subsequently, 50 g of $TiO_2/ZrO_2$ support ($ZrO_2$ (15%) on $TiO_2$ (anatase), Huntsman, d50=about 40 µm) are added all at once while stirring (400 rpm). The suspension thus obtained is stirred at 70° C. for 60 min, keeping the pH constant at 7.5. The pH rises into the basic range during this period and is kept at 7.5 with 2.0 M $HNO_3$ solution and 0.5 M $Na_2CO_3$ solution. The suspension is vacuum-filtered while still hot through a suction filter and washed 5 times with 250 ml of dist. water each time (5 ml of dist. water/g of support). The residual conductivity of the wash water obtained is to be below 100 µS/cm². The catalyst obtained is dried in a thin layer at 120° C. for 16 h. The catalyst is heated to 70° C. under nitrogen and then reduced with a stream of 5% by volume of $H_2$ in $N_2$ and cooled down to room temperature, and the gas stream is ended. The performance of the catalyst was evaluated in a batch test; see Table 1.

Example 17

Preparation of an Au Catalyst on $TiO_2/SiO_2$ Support

In a glass flask with mechanical stirring, 1.82 g of auric acid ($HAuCl_4*3H_2O$) are dissolved in 600 g of water and heated to internal temperature 70° C. The pH of the solution thus obtained is about 2.2 and is adjusted to 7.5 with 0.5 M $Na_2CO_3$ solution and then maintained over a period of 10 minutes. Subsequently, 50 g of $TiO_2/SiO_2$ support ($SiO_2$ (8.5%) on $TiO_2$ (anatase), Huntsman, d50=about 40 µm) are added all at once while stirring (400 rpm). The suspension thus obtained is stirred at 70° C. for 60 min, keeping the pH constant at 7.5. The pH rises into the basic range during this period and is kept at 7.5 with 2.0 M $HNO_3$ solution and 0.5 M $Na_2CO_3$ solution. The suspension is vacuum-filtered while still hot through a suction filter and washed 5 times with 250 ml of dist. water each time (5 ml of dist. water/g of support). The residual conductivity of the wash water obtained is to be below 100 µS/cm². The catalyst obtained is dried in a thin layer at 120° C. for 16 h. The catalyst is heated to 70° C. under nitrogen and then reduced with a stream of 5% by volume of $H_2$ in $N_2$ and cooled down to room temperature, and the gas stream is ended. The performance of the catalyst was evaluated in a batch test; see Table 1.

Example 18

Preparation of an Au Catalyst on $TiO_2/Al_2O_3$ Support

In a glass flask with mechanical stirring, 1.82 g of auric acid ($HAuCl_4*3H_2O$) are dissolved in 600 g of water and heated to internal temperature 70° C. The pH of the solution thus obtained is about 2.2 and is adjusted to 7.5 with 0.5 M $Na_2CO_3$ solution and then maintained over a period of 10 minutes. Subsequently, 50 g of $TiO_2/Al_2O_3$ support ($Al_2O_3$ (8.6%) on $TiO_2$ (anatase), Huntsman, d50=about 40 µm) are added all at once while stirring (400 rpm). The suspension thus obtained is stirred at 70° C. for 60 min, keeping the pH constant at 7.5. The pH rises into the basic range during this period and is kept at 7.5 with 2.0 M $HNO_3$ solution and 0.5 M $Na_2CO_3$ solution. The suspension is vacuum-filtered while still hot through a suction filter and washed 5 times with 250 ml of dist. water each time (5 ml of dist. water/g of support). The residual conductivity of the wash water obtained is to be below 100 µS/cm². The catalyst obtained is dried in a thin layer at 120° C. for 16 h. The catalyst is heated to 70° C. under nitrogen and then reduced with a stream of 5% by volume of $H_2$ in $N_2$ and cooled down to room temperature, and the gas stream is ended. The performance of the catalyst was evaluated in a batch test; see Table 1.

Example 19

Preparation of an Au Catalyst on $TiO_2$ (Rutile) Support

In a glass flask with mechanical stirring, 1.82 g of auric acid ($HAuCl_4*3H_2O$) are dissolved in 600 g of water and heated to internal temperature 70° C. The pH of the solution thus obtained is about 2.2 and is adjusted to 7.5 with 0.5 M $Na_2CO_3$ solution and then maintained over a period of 10 minutes. Subsequently, 50 g of $TiO_2$ ($TiO_2$ (rutile), Huntsman, d50=about 40 µm) are added all at once while stirring (400 rpm). The suspension thus obtained is stirred at 70° C. for 60 min, keeping the pH constant at 7.5. The pH rises into the basic range during this period and is kept at 7.5 with 2.0 M $HNO_3$ solution and 0.5 M $Na_2CO_3$ solution. The suspension is vacuum-filtered while still hot through a suction filter and washed 5 times with 250 ml of dist. water each time (5 ml of dist. water/g of support). The residual conductivity of the wash water obtained is to be below 100 µS/cm². The catalyst obtained is dried in a thin layer at 120° C. for 16 h. The catalyst is heated to 70° C. under nitrogen and then reduced with a stream of 5% by volume of $H_2$ in $N_2$ and cooled down to room temperature, and the gas stream is ended. The performance of the catalyst was evaluated in a batch test; see Table 1.

Example 20

Comparative Example 1

Ni—Au Catalyst

According to the patent literature (EP2210664, Ex. 1), a nickel-gold catalyst was prepared. The performance of the catalyst was evaluated in a batch test (see Table 1) and continuously (see Table 2).

Example 21

Comparative Example 2

Co—Au Catalyst

According to the patent literature (WO2017084969, Ex. 4), a cobalt-gold catalyst was prepared. Performance of the catalyst was evaluated in a batch test (see Table 1) and continuously (see Table 2).

Example 22

The batch size from Example 2 was scaled up by a factor of seven and reproduced a total of three times with 350 g of support used. The activity and selectivity of the individual reproductions—even by comparison with Example 2—did not result in any scatter beyond the limit of measurement accuracy. The catalyst batches thus obtained were combined and mixed, and 600 g that were taken from this mixture were initially charged in a 20 l tank.

Figure 2:
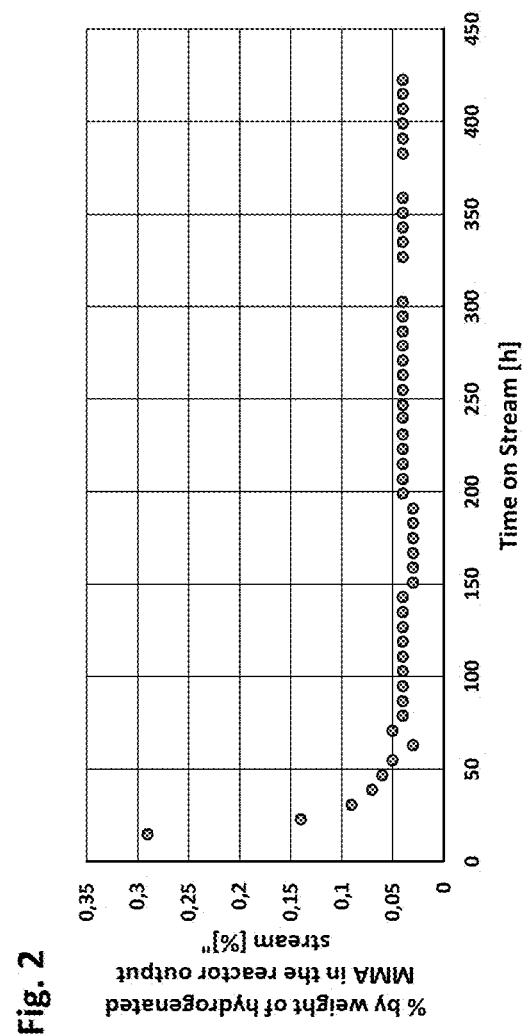
FIG. 2 shows, for Table 4, the dependence of the formation of the hydrogenated MMA by-product depending on the experimental run time in continuous operation.
Figure 3:
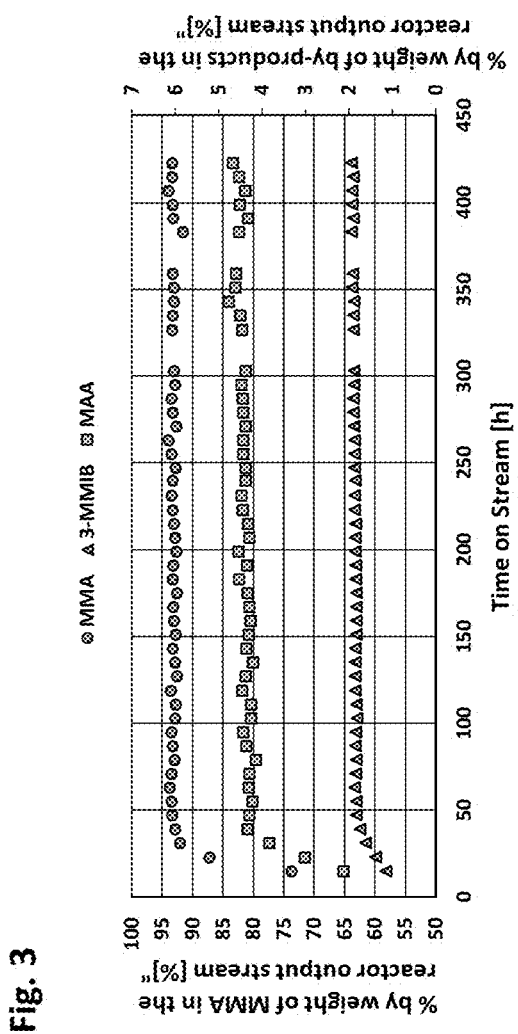
FIG. 3 shows, for Table 4, the composition of the reactor output stream for components present in a concentration greater than 1% by weight in continuous operation.
Figure 4:
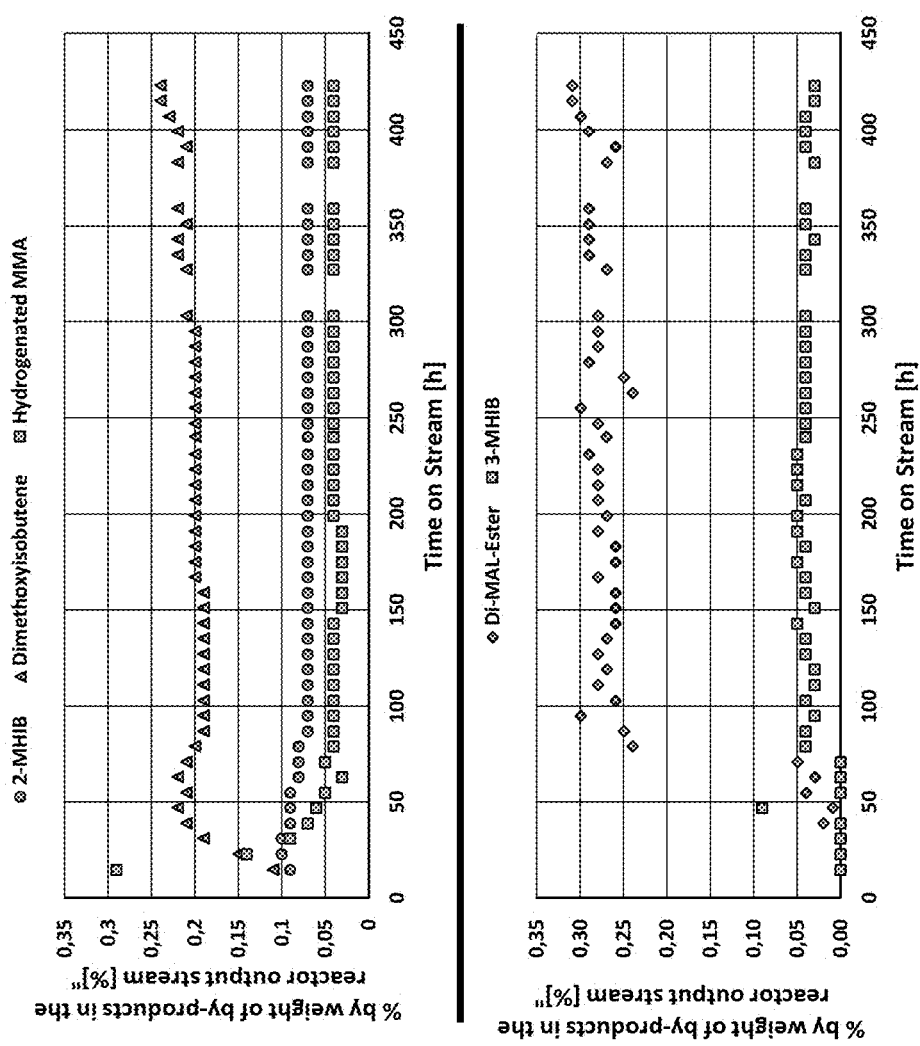
FIG. 4 shows, for Table 4, the composition of the reactor output stream for components present in a concentration less than 1% by weight in continuous operation.

Methacrolein is fed continuously at a constant rate of 500 g/h into the 20 l stirred tank reactor that was sparged from below (sparging with air up to a residual oxygen content of up to 4% by volume in the offgas) under a pressure of 5 bar and at internal temperature 80° C. For every mole of methacrolein fed in, 4 mol of methanol were simultaneously fed into the reactor, and this ratio was always kept constant. At the same time, a sufficient amount of NaOH solution (in nnethanol/$H_2O$ (95:5)) was fed into this reactor that the value in the reactor remained constant at pH=7. The reaction mixture was withdrawn continuously from the reactor via a filter. After the time specified in Table 4, the product samples were taken and analysed by means of GC and HPLC. The value for methacrylic acid in particular can be determined particularly precisely in this way, even in the form of its sodium salt formed in situ. The formation of methyl isobutyrate drops very significantly within the first two days and, after about four days, reaches a steady-state value of 50 ppm which remains substantially constant over the entire duration of the experiment. The activity is constantly stable and high. Table 4 and FIGS. 1 to 4.

Batch Tests for MMA Preparation (Details of Table 1)

A gold-containing catalyst according to one of Examples 1 to 21 (384 mg), methacrolein (1.20 g) and methanol (9.48 g) were stirred at internal temperature 60° C. and a pressure of 30 bar in an atmosphere of 7% by volume of $O_2$ in $N_2$ in a 140 ml steel autoclave with a magnetic stirrer for 2 h. After 2 h, the mixture was cooled down, degassed, filtered and analysed by means of GC. Each catalyst was tested at least twice under identical conditions; the results of the respective experiments were averaged. The resulting conversion of methacrolein (C(MAL), in %) and the selectivity for MMA (S(MMA), in %) for every catalyst tested are collated in Table 1 below.

Continuous Test for Preparation of MMA (General Description for Table 2)

The pH of a 42.5% by weight solution of MAL in methanol is adjusted to pH=7 while stirring by the addition of a 1% by weight solution of NaOH in methanol. This solution is fed continuously at a constant rate of addition to a stirred and sparged stirred tank reactor (sparging with air) under pressure of 10 bar and at internal temperature of 80° C. At the same time, this reactor containing 20 g of powder catalyst (from a previous example) is fed with a sufficient amount of 1% by weight NaOH solution (in methanol) that the value pH=7 in the reactor remains constant. The reaction mixture was withdrawn continuously from the reactor via a filter. After the time specified in Table 2, the product samples were taken and analysed by means of GC.

TABLE 1

Catalyst evaluation by batch test

| | Ex. No. | Catalyst | Variation | Conversion [MAL] | Selectivity [MMA] |
|---|---|---|---|---|---|
| Catalyst grain | 1 | 1.4% Au on TiO2 | P25, Evonik Industries | 93.1% | 94.9% |
| | 2 | 1.4% Au on TiO2 | Hombikat, Huntsman | 91.7% | 90.9% |
| | 3 | 1.1% Au on TiO2 | P25 H6, Evonik Industries (recalcined) | 95.3% | 91.0% |
| | 4 | 1% Au on TiO2 | pelletized & recalcined --> without mortar crushing 2 × 5 mm | 75.1% | 93.2% |
| | 5 | 1% Au on TiO2 | mortar-crushed and sieved to 36-100 μm | 87.8% | 93.0% |
| | 6 | 1% Au on TiO2 | mortar-crushed and sieved to <36 μm | 88.5% | 92.7% |
| Calcination method | 7 | 1.4% Au on TiO2 | uncalcined | 33.1% | 96.6% |
| | 8 | 1.4% Au on TiO2 | calcined 3 h, 70° C., N2, H2 stream | 92.7% | 93.0% |
| | 9 | 1.4% Au on TiO2 | calcined 4.5 h, 70° C., N2, H2 stream | 93.2% | 91.1% |
| | 10 | 1.4% Au on TiO2 | 2% by weight of formate in methanol | 68.4% | 89.1% |
| | 11 | 1.4% Au on TiO2 | 2% by weight of formate in water | | |
| | 12 | 1.4% Au on TiO2 | 1 h, in MeOH with O2 | 96.1% | 93.4% |
| | 13 | 1.4% Au on TiO2 | 1 h, in MeOH with N2 | | |
| Amount of gold | 14 | 0.7% Au on TiO2 | Hombikat, Huntsman | 70.2% | 87.9% |
| | 15 | 0.1% Au on TiO2 | Hombikat, Huntsman | 18.4% | 58.7% |
| Mixed support | 16 | Au on TiO2/ZrO2 | Huntsman, support | 65.9% | 81.1% |
| | 17 | Au on TiO2/SiO2 | Huntsman, support | | |
| | 18 | Au on TiO2/Al2O3 | Huntsman, support | | |
| | 19 | Au on TiO2 (rutile) | Huntsman, support | | |
| Comparison | 20 | NiAu on SiO/Al2O3/MgO | EP2210664, Ex. 1 | 81.3% | 93.2% |
| | 21 | CoAu on SiO/Al2O3/MgO | WO2017084969, Ex. 4 | 80.1% | 93.2% |

TABLE 2

Catalyst evaluation by continuous testing

| Cat. from Ex. No. | Catalyst | TOS [h] | Conversion % [MAL] | Selectivity % [MMA] | Selectivity % [hydrogenated MMA] | Batch test No. (reference) |
|---|---|---|---|---|---|---|
| 2 | 1.4% Au on TiO2 | 21 | 77.1 | 92.1 | 0.05 | 2 |
|   |   | 495 | 77.89 | 92.4 | 0.01 |   |
|   |   | 999 | 78.5 | 91.3 | 0.01 |   |
| 5 | 1.0% Au on TiO2, mortar-crushed | 28 | 85.1 | 92.2 | 0.06 | 5 |
|   |   | 77 | 83.1 | 92.1 | 0.01 |   |
|   |   | 240 | 78.2 | 92 | 0.01 |   |
|   |   | 500 | 71.3 | 92.1 | 0.01 |   |
| 20 | NiAu catalyst | 22 | 75.1 | 92 | 0.01 | 20 |
|   |   | 525 | 74.8 | 91.9 | 0.13 |   |
|   |   | 676 | 74.6 | 92.1 | 0.12 |   |
|   |   | 1000 | 74.1 | 91.9 | 0.13 |   |
| 21 | CoAu catalyst | 50 | 73.5 | 92.3 | 0.02 | 21 |
|   |   | 200 | 71.09 | 91.8 | 0.08 |   |
|   |   | 380 | 70.8 | 91.5 | 0.09 |   |
|   |   | 480 | 70.6 | 92.1 | 0.08 |   |

Continuous Test for Preparation of MMA at Varied pH (Description for Table 3)

The pH of a 42.5% by weight solution of MAL in methanol is adjusted to pH=7 while stirring by the addition of a 1% by weight solution of NaOH in methanol. This solution is fed continuously at a constant rate of addition to a stirred and sparged stirred tank reactor (sparging with air) under pressure of 10 bar and at internal temperature of 80° C. At the same time, this reactor containing 20 g of powder catalyst from Example 2 is fed with a sufficient amount of 1% by weight NaOH solution (in methanol) that the pH in the reactor remained at a constant setting of the value mentioned in Table 3. The reaction mixture was withdrawn continuously from the reactor via a filter. At least three product samples (with delay time 24 h) were taken in each case and analysed by means of GC before the pH was varied.

TABLE 3

| Cat. from Ex. No. | Catalyst | pH | Conversion % [MAL] | Selectivity % [MMA] | Selectivity % [DiMAL & DiMAL ester] | Selectivity % [dimethoxy-isobutene] | Selectivity % [3-MMIB] |
|---|---|---|---|---|---|---|---|
| 2 | 1.4% Au on TiO2 | 6.6 | 78.7% | 91.7% | 0.248% | 0.228% | 0.792% |
|   |   | 7.0 | 86.3% | 92.4% | 0.084% | 0.064% | 0.813% |
|   |   | 7.6 | 92.2% | 93.0% | 0.037% | 0.017% | 0.879% |
|   |   | 8.0 | 96.8% | 91.9% | 0.011% | 0.007% | 0.912% |
|   |   | 8.3 | 98.1% | 92.1% | 0.012% | 0.001% | 0.961% |

TABLE 4

| hr TOS | % MAL Conversion | wt. % Hydrogenated MMA | wt. % MMA | wt. % 2-MHIB | wt. % Dimethoxy-isobutene | wt. % MAA | wt. % 3-MMIB | wt. % 3-MHIB | wt. % Di-MAL ester | wt. % Sum C4 Selectivities | hr Residence Time | mol MAL hr · kg · cat WHSV | mol MMA hr · kg · cat STY | mol/mol MeOH/MAL in feed | mol/mol MeOH/MAL in reactor | mol/mol H2O/MAL in reactor |
|---|---|---|---|---|---|---|---|---|---|---|---|---|---|---|---|---|
| \multicolumn{17}{|c|}{Continuous reaction regime in a 20 l pressure reactor.} |||||||||||||||||
| 14.75 | 82.32% | 0.29% | 73.64% | 0.09% | 0.11% | 2.12% | 1.14% | 0.00% | 0.00% | 77.16% | 8.74 | 11.51 | 7.11 | 4.05 | 22.31 | 4.81 |
| 22.75 | 77.75% | 0.14% | 87.18% | 0.10% | 0.15% | 3.01% | 1.38% | 0.00% | 0.00% | 91.82% | 8.78 | 11.52 | 8.12 | 4.05 | 15.77 | 3.63 |
| 30.75 | 75.13% | 0.09% | 92.06% | 0.09% | 0.19% | 3.82% | 1.62% | 0.00% | 0.00% | 97.82% | 8.77 | 11.50 | 8.31 | 4.06 | 13.50 | 3.15 |
| 38.75 | 75.00% | 0.07% | 92.85% | 0.09% | 0.21% | 4.33% | 1.75% | 0.00% | 0.02% | 99.32% | 8.77 | 11.52 | 8.39 | 4.05 | 13.47 | 3.32 |
| 46.75 | 74.34% | 0.06% | 93.32% | 0.09% | 0.22% | 4.28% | 1.82% | 0.00% | 0.01% | 99.89% | 8.78 | 11.51 | 8.34 | 4.06 | 13.22 | 3.27 |
| 54.75 | 74.36% | 0.05% | 93.40% | 0.09% | 0.21% | 4.21% | 1.82% | 0.00% | 0.04% | 99.82% | 8.78 | 11.50 | 8.35 | 4.05 | 12.61 | 2.89 |
| 62.75 | 74.55% | 0.05% | 93.72% | 0.08% | 0.22% | 4.30% | 1.87% | 0.00% | 0.03% | 100.25% | 8.78 | 11.48 | 8.39 | 4.06 | 13.15 | 2.96 |
| 70.75 | 74.60% | 0.05% | 93.39% | 0.08% | 0.21% | 4.25% | 1.84% | 0.00% | 0.03% | 99.90% | 8.78 | 11.52 | 8.39 | 4.05 | 12.95 | 3.01 |
| 78.75 | 74.37% | 0.04% | 92.89% | 0.08% | 0.20% | 4.13% | 1.83% | 0.04% | 0.05% | 99.41% | 8.78 | 11.55 | 8.33 | 4.04 | 13.07 | 3.43 |
| 86.75 | 74.25% | 0.04% | 93.19% | 0.07% | 0.19% | 4.36% | 1.85% | 0.04% | 0.24% | 99.98% | 8.78 | 11.55 | 8.34 | 4.05 | 13.06 | 3.52 |
| 94.75 | 74.24% | 0.04% | 93.40% | 0.07% | 0.19% | 4.42% | 1.84% | 0.03% | 0.25% | 100.28% | 8.78 | 11.51 | 8.34 | 4.06 | 13.14 | 3.50 |
| 102.75 | 74.26% | 0.04% | 92.84% | 0.07% | 0.19% | 4.24% | 1.81% | 0.04% | 0.30% | 99.49% | 8.77 | 11.51 | 8.31 | 4.05 | 13.10 | 3.51 |
| 110.75 | 74.45% | 0.04% | 92.76% | 0.07% | 0.19% | 4.25% | 1.83% | 0.03% | 0.26% | 99.45% | 8.78 | 11.55 | 8.33 | 4.05 | 13.19 | 3.58 |
| 118.75 | 74.15% | 0.04% | 93.49% | 0.07% | 0.19% | 4.45% | 1.85% | 0.03% | 0.28% | 100.39% | 8.78 | 11.51 | 8.34 | 4.06 | 13.11 | 3.53 |
| 126.75 | 74.12% | 0.04% | 92.53% | 0.07% | 0.19% | 4.37% | 1.85% | 0.04% | 0.28% | 99.37% | 8.77 | 11.55 | 8.26 | 4.05 | 13.02 | 3.41 |
| 134.75 | 74.21% | 0.03% | 92.82% | 0.07% | 0.19% | 4.20% | 1.86% | 0.04% | 0.27% | 99.49% | 8.78 | 11.55 | 8.29 | 4.05 | 13.08 | 3.55 |
| 142.75 | 74.15% | 0.03% | 93.20% | 0.07% | 0.19% | 4.35% | 1.85% | 0.05% | 0.26% | 99.99% | 8.78 | 11.53 | 8.31 | 4.05 | 12.88 | 3.57 |
| 150.75 | 74.19% | 0.03% | 92.67% | 0.07% | 0.19% | 4.30% | 1.83% | 0.03% | 0.26% | 99.40% | 8.78 | 11.55 | 8.25 | 4.05 | 12.86 | 3.39 |
| 158.75 | 74.11% | 0.03% | 92.99% | 0.07% | 0.19% | 4.26% | 1.82% | 0.04% | 0.26% | 99.67% | 8.78 | 11.54 | 8.27 | 4.05 | 12.92 | 3.36 |
| 166.75 | 74.15% | 0.03% | 93.15% | 0.07% | 0.20% | 4.29% | 1.83% | 0.04% | 0.28% | 99.86% | 8.78 | 11.53 | 8.30 | 4.05 | 13.06 | 3.39 |
| 174.75 | 74.18% | 0.03% | 92.55% | 0.07% | 0.20% | 4.33% | 1.82% | 0.05% | 0.26% | 99.31% | 8.78 | 11.55 | 8.22 | 4.05 | 12.87 | 3.36 |
| \multicolumn{17}{|c|}{run time 182 h-358 h} |||||||||||||||||
| 182.75 | 74.21% | 0.03% | 93.17% | 0.07% | 0.20% | 4.52% | 1.84% | 0.04% | 0.26% | 100.11% | 8.78 | 11.54 | 8.27 | 4.05 | 12.95 | 3.45 |
| 190.75 | 74.25% | 0.04% | 93.14% | 0.07% | 0.20% | 4.34% | 1.84% | 0.05% | 0.28% | 99.93% | 8.78 | 11.56 | 8.28 | 4.05 | 12.90 | 3.36 |
| 198.75 | 74.18% | 0.04% | 92.66% | 0.07% | 0.20% | 4.53% | 1.86% | 0.05% | 0.27% | 99.66% | 8.78 | 11.54 | 8.19 | 4.05 | 12.80 | 3.42 |
| 206.75 | 74.21% | 0.04% | 92.85% | 0.07% | 0.20% | 4.31% | 1.86% | 0.04% | 0.28% | 99.58% | 8.78 | 11.55 | 8.18 | 4.06 | 12.66 | 3.34 |
| 214.75 | 74.19% | 0.04% | 93.01% | 0.07% | 0.20% | 4.43% | 1.84% | 0.05% | 0.28% | 99.79% | 8.77 | 11.55 | 8.24 | 4.05 | 12.87 | 3.51 |
| 222.75 | 74.19% | 0.04% | 93.17% | 0.07% | 0.20% | 4.44% | 1.87% | 0.05% | 0.28% | 100.14% | 8.78 | 11.51 | 8.18 | 4.05 | 12.74 | 3.38 |
| 230.75 | 74.10% | 0.04% | 93.40% | 0.07% | 0.20% | 4.47% | 1.87% | 0.05% | 0.29% | 100.38% | 8.78 | 11.50 | 8.18 | 4.06 | 12.64 | 3.35 |
| 239.25 | 74.18% | 0.04% | 93.25% | 0.07% | 0.20% | 4.37% | 1.86% | 0.05% | 0.27% | 100.06% | 8.78 | 11.54 | 8.24 | 4.04 | 12.72 | 3.29 |
| 246.75 | 74.24% | 0.04% | 92.68% | 0.07% | 0.20% | 4.37% | 1.87% | 0.04% | 0.28% | 99.50% | 8.78 | 11.55 | 8.12 | 4.04 | 12.49 | 3.31 |
| 254.75 | 74.23% | 0.04% | 93.39% | 0.07% | 0.20% | 4.42% | 1.87% | 0.04% | 0.30% | 100.30% | 8.78 | 11.52 | 8.15 | 4.06 | 12.47 | 3.26 |
| 262.75 | 74.12% | 0.04% | 93.92% | 0.07% | 0.20% | 4.42% | 1.87% | 0.04% | 0.24% | 100.77% | 8.78 | 11.51 | 8.21 | 4.05 | 12.55 | 3.25 |
| 270.75 | 74.31% | 0.04% | 92.63% | 0.07% | 0.20% | 4.37% | 1.88% | 0.04% | 0.25% | 99.45% | 8.78 | 11.52 | 8.06 | 4.06 | 12.66 | 3.23 |
| 278.75 | 74.24% | 0.04% | 93.20% | 0.07% | 0.20% | 4.43% | 1.88% | 0.04% | 0.28% | 100.14% | 8.79 | 11.48 | 8.08 | 4.05 | 12.40 | 3.22 |
| 286.75 | 74.19% | 0.04% | 93.43% | 0.07% | 0.20% | 4.24% | 1.90% | 0.04% | 0.29% | 100.35% | 8.78 | 11.53 | 8.08 | 4.06 | 12.47 | 3.28 |
| 294.75 | 74.11% | 0.04% | 92.81% | 0.07% | 0.20% | 4.44% | 1.89% | 0.04% | 0.28% | 99.75% | 8.79 | 11.52 | 8.12 | 4.04 | 12.74 | 3.21 |
| 302.75 | 74.15% | 0.04% | 92.97% | 0.07% | 0.21% | 4.46% | 1.88% | 0.04% | 0.28% | 99.81% | 8.78 | 11.55 | 8.05 | 4.05 | 12.64 | 3.27 |
| 310.75 | 74.24% | 0.04% | 93.33% | 0.07% | 0.20% | 4.37% | 1.88% | 0.04% | 0.27% | 100.29% | 8.78 | 11.52 | 8.05 | 4.05 | 12.50 | 3.76 |
| 326.75 | 74.27% | 0.04% | 93.24% | 0.07% | 0.21% | 4.45% | 1.90% | 0.04% | 0.28% | 100.20% | 8.78 | 11.55 | 8.08 | 4.03 | 12.71 | 3.65 |
| 334.75 | 74.30% | 0.04% | 93.06% | 0.07% | 0.22% | 4.50% | 1.90% | 0.04% | 0.29% | 100.11% | 8.79 | 11.56 | 8.11 | 4.03 | 12.54 | 3.67 |
| 342.75 | 74.24% | 0.04% | 93.00% | 0.07% | 0.21% | 4.76% | 1.88% | 0.03% | 0.29% | 100.24% | 8.78 | 11.55 | 8.09 | 4.03 | 12.73 | 3.66 |
| 358.75 | 74.24% | 0.04% | 93.17% | 0.07% | 0.22% | 4.59% | 1.91% | 0.04% | 0.29% | 100.45% | 8.78 | 11.53 | 8.05 | 4.04 | 12.62 | 3.66 |

TABLE 4-continued

| hr TOS | % MAL Conversion | wt. % Hydrogenated MMA | wt. % MMA | wt. % 2-MHIB | wt. % Dimethoxy-isobutene | wt. % MAA | wt. % 3-MMIB | wt. % 3-MHIB | wt. % Di-MAL ester | wt. % Total C4 selectivity | hr Residence time | mol MAL/ hr · kg · cat WHSV | mol MMA/ hr · kg · cat STY | mol/mol MeOH/MAL in feed | mol/mol MeOH/MAL in reactor | mol/mol H2O/MAL in reactor |
|---|---|---|---|---|---|---|---|---|---|---|---|---|---|---|---|---|
| | | | | | | | run time 382 h-422 h | | | | | | | | | |
| 382.75 | 74.15% | 0.04% | 91.52% | 0.07% | 0.22% | 4.52% | 1.94% | 0.03% | 0.27% | 98.04% | 8.78 | 11.52 | 8.00 | 4.05 | 12.82 | 3.47 |
| 390.75 | 74.33% | 0.04% | 93.16% | 0.07% | 0.21% | 4.32% | 1.90% | 0.04% | 0.26% | 99.96% | 8.78 | 11.50 | 8.04 | 4.07 | 12.53 | 3.53 |
| 398.75 | 74.25% | 0.04% | 93.25% | 0.07% | 0.22% | 4.51% | 1.93% | 0.04% | 0.29% | 100.24% | 8.78 | 11.50 | 8.01 | 4.05 | 12.63 | 3.52 |
| 406.75 | 74.33% | 0.04% | 93.88% | 0.07% | 0.23% | 4.38% | 1.93% | 0.04% | 0.30% | 100.76% | 8.78 | 11.52 | 8.04 | 4.04 | 12.67 | 3.46 |
| 414.75 | 74.15% | 0.04% | 93.26% | 0.07% | 0.24% | 4.52% | 1.89% | 0.03% | 0.31% | 100.83% | 8.78 | 11.51 | 7.96 | 4.04 | 12.73 | 3.44 |
| 422.75 | 74.19% | 0.04% | 93.35% | 0.07% | 0.24% | 4.66% | 1.94% | 0.03% | 0.31% | 100.62% | 8.79 | 11.51 | 7.97 | 4.04 | 12.65 | 3.49 |

Key:
TOS = time on stream; MAL conversion = conversion of methacrolein; Hydrogenated MMA = methyl isobutyrate; MMA = methyl methacrylate; 2-MHIB = methyl 2-hydroxyisobutyrate; MAA = methacrylic acid; 3-MMIB = methyl 3-methoxyisobutyrate; 3-MHIB = methyl 3-hydroxyisobutyrate;

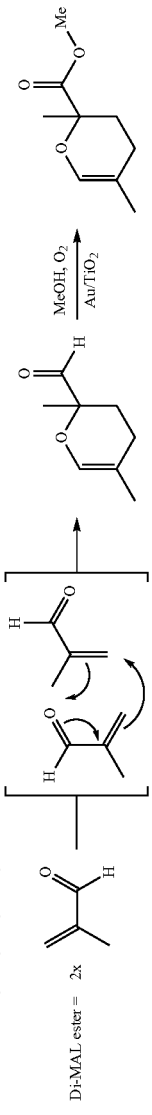

Diels-Alder dimerization product of methacrolein after direct oxidation of the aldehyde to the ester.

The invention claimed is:

1. A process for preparing a carboxylic ester from an aldehyde, the process comprising:
   continuously conducting an oxidative esterification of the aldehyde to the carboxylic ester via heterogeneous catalysis in a liquid phase in the presence of a catalyst particle,
   wherein a content of hydrogenated by-product in the carboxylic ester is from 50 ppm to 100 ppm,
   wherein the catalyst particle consists of 0.1% to 3% by weight of gold, 25% to 99.8% by weight of $TiO_2$, 0% to 25% by weight of at least one oxide of an alkali metal, an alkaline earth metal, a rare earth metal, and zirconium, 0% to 20% by weight of at least one oxide selected from the group consisting of an iron oxide, a zinc oxide, and a cobalt oxide, and 0% to 5% by weight of at least one other component;
   gold, optionally together with the iron oxide, zinc oxide, and/or cobalt oxide, is bound to the catalyst particle in the form of particles having an average diameter between 2 and 10 nm; and the catalyst particle has an average geometric equivalent diameter between 5 μm and 10 mm, and
   more than 90% of the gold is present in an outer region of the catalyst particle, wherein the outer region makes up a maximum of 60% of the geometric equivalent diameter of the catalyst particle,
   wherein the catalyst particle does not contain silicon oxide and/or $Al_2O_3$.

2. The process according to claim 1, wherein the catalyst particle consists of 0.3% to 2.5% by weight of gold, 50% to 99.5% by weight of $TiO_2$, 0% to 10% by weight of the at least one oxide selected from the group consisting of an iron oxide, a zinc oxide and a cobalt oxide, and 0% to 5% by weight of the at least one other component.

3. The process according to claim 1, wherein the catalyst particle consists of 0.3% to 2.5% by weight of gold, 96% to 99.5% by weight of $TiO_2$ and not more than 3.7% by weight of other components.

4. The process according to claim 1, wherein the catalyst particles are porous and have a specific surface area between 20 and 300 $m^2/g$ and an average pore diameter of 2 to 30 rim.

5. The process according to claim 4, wherein the specific surface area of the catalyst particles is between 30 and 200 $m^2/g$, and the average pore diameter is 5 to 25 nm.

6. The process according to claim 1, wherein the oxidative esterification is conducted in the presence of oxygen and an alcohol.

7. The process according to claim 6, wherein the aldehyde is methacrolein and the carboxylic ester is an alkyl methacrylate.

8. The process according to claim 7, wherein the alcohol is methanol; methacrolein continuously reacts with methanol in the presence of an oxygenous gas at a reaction temperature between 40-120° C., an absolute pressure between 1 and 20 bar, and with a slurry density of the catalyst, which is being stirred and swirled in a steady-state product mixture comprising MMA, methacrolein, methanol and water, between 1% and 20% by weight; and methacrolein is not fully converted in at least one reactor in each case, but after a partial conversion between 20% and 95% is separated continuously from the catalyst via filtration and fed to a workup.

9. The process according to claim 8, wherein air is supplied continuously to the reactor as the oxygenous gas and an oxygen content of gas phase that forms the reaction mixture is between 2% and 8% by volume.

10. The process according to claim 8, wherein the reaction is conducted at a reaction temperature between 50° C. and 100° C. at an absolute pressure between 2 and 15 bar.

11. The process according to claim 8, wherein the slurry density of the catalyst is between 2% and 15% by weight.

12. The process according to claim 8, wherein methacrolein is not fully converted in one reactor in each case or multiple reactors connected in series, but after a partial conversion between 40% and 80% is separated continuously from the catalyst via filtration and fed to the workup.

* * * * *